United States Patent
Baity

(10) Patent No.: US 10,697,951 B2
(45) Date of Patent: Jun. 30, 2020

(54) IN-SOIL DATA MONITORING SYSTEM AND METHOD

(71) Applicant: AAI Corporation, Hunt Valley, MD (US)

(72) Inventor: Sean M. Baity, Westminster, MD (US)

(73) Assignee: Textron Systems Corporation, Hunt Valley, MD (US)

( * ) Notice: Subject to any disclaimer, the term of this patent is extended or adjusted under 35 U.S.C. 154(b) by 556 days.

(21) Appl. No.: 14/569,829

(22) Filed: Dec. 15, 2014

(65) Prior Publication Data

US 2016/0169855 A1    Jun. 16, 2016

(51) Int. Cl.
*G01N 33/24*    (2006.01)

(52) U.S. Cl.
CPC ........ *G01N 33/24* (2013.01); *B64C 2201/123* (2013.01); *G01N 2033/245* (2013.01)

(58) Field of Classification Search
CPC ...... G01S 13/89; G01S 13/888; G01S 13/885; A01G 25/167; A01C 23/04; A01C 21/005; A01B 79/005; A01B 69/00; G01C 21/32; G05D 1/0225; G05D 2201/0201
USPC ................ 47/58.1 SC; 701/2, 50; 455/556.1; 700/169, 179, 175; 180/331; 73/863.01, 73/863.21
See application file for complete search history.

(56) References Cited

U.S. PATENT DOCUMENTS

| | | | |
|---|---|---|---|
| 5,302,957 A * | 4/1994 | Franzen | G01S 11/02 342/125 |
| 6,484,652 B1 | 11/2002 | Colburn, Jr. | |
| 6,937,939 B1 | 8/2005 | Shibusawa et al. | |
| 7,103,451 B2 | 9/2006 | Seal et al. | |
| 8,671,969 B2 | 3/2014 | Dresselhaus et al. | |
| 8,763,478 B2 * | 7/2014 | Riess | G01N 1/02 73/863.21 |
| 9,251,698 B2 * | 2/2016 | Vian | H04Q 9/00 |
| 2006/0022800 A1 * | 2/2006 | Krishna | G06K 7/0008 340/10.2 |
| 2014/0024313 A1 | 1/2014 | Campbell | |

FOREIGN PATENT DOCUMENTS

| | | |
|---|---|---|
| EP | 2612110 A1 | 7/2013 |
| WO | 2014113460 A1 | 7/2014 |
| WO | WO 2014113460 A1 * | 7/2014 ............. G01N 33/24 |

OTHER PUBLICATIONS

North Dakota State University, NDSU-Developed Biodegradable Soil Sensor Can Be "Planted" with a Seed Mixture, Tech Transfer Times, Spring 2013, vol. 4.

* cited by examiner

*Primary Examiner* — Peter M Poon
*Assistant Examiner* — Jeffrey R Larsen
(74) *Attorney, Agent, or Firm* — BainwoodHuang

(57) ABSTRACT

An in soil data collection and analysis system and process is disclosed where the data from a plurality of in soil sensors is combined with other data that is acquired by an unmanned aerial vehicle (UAV) to create a fused data set that can be used to determine an appropriate corrective action or response to the fused data.

22 Claims, 3 Drawing Sheets

IN-SOIL DATA MONITORING SYSTEM AND METHOD

OVERVIEW OF INVENTION

1. Technical Field

The present disclosure relates generally to apparatus, systems and methods for in-soil data monitoring, data capture and data fusion. More specifically, the disclosure relates to an in-soil data monitoring system employing an unmanned vehicle (UV) and a wireless soil sensor for use in agricultural and chemical spill settings for improved high resolution alerts and corrective actions.

2. Background

Current methods of assessing crop health rely on monitoring spectral content of light reflected by the plants. Commonly referred to as remote sensing, these methods use passive sensors on satellites and aircraft or active sensors mounted on tractors. There are drawbacks to these methods in that many variables can impact reflectivity including nutrient deficiencies, differences among varieties, field resolution, disease, etc. In particular, soil type is one of the more significant variables in using this method of nutrient sensing. While these tools are useful in examining crop health, they are indirect measurements and ultimately require previous knowledge of the soil conditions and specialized algorithms to properly evaluate crop conditions.

In order to address these inherent deficiencies associated with remote sensing and spectral monitoring, a very small, biodegradable soil sensor has been developed, which is disclosed in patent number WO 2014/113460 A1 entitled Biodegradable Soil Sensor, Systems and Method, which is incorporated herein by reference in its entirety. The biodegradable soil sensor is essentially mixed in with the seed of the crop and is planted along with the seed in the soil. The seed is configured to measure various data associated with crop health and wirelessly transmit that data for collection and analysis in order to determine if corrective actions (such as for example more water or fertilizer) may be necessary to improve crop health. While this patent application does mention the use of aerial vehicles for the collection of the data from the soil sensor, there is no discussion or teaching on how the data is to be correlated and analyzed in order to determine the best corrective actions.

Therefore, it is an object, feature, or advantage of the present disclosure to provide a system for the collection and analysis of biodegradable soil sensors for measuring crop health that is configured to take direct measurements from the soil and further analyze and correlate that data in order to obtain an appropriate corrective action to improve crop health.

The soil sensors mentioned above could also be used to monitor areas for chemical spills or other bio-hazardous events by planting the sensors in the ground adjacent for example a buried pipe line or the like. The soil sensor may be configured to detect the presence of a specific chemical and wirelessly transmit an alert to an overflying aerial vehicle or ground vehicle.

While there are commercially available products that directly measure the presence of a chemical, these sensors are typically large, bulky, and expensive. This means that fewer sensors are available within a particular area generating low resolution data which may not give accurate information about conditions throughout a particular area and may not detect spills immediately which could result in catastrophic environmental damage.

Therefore, another object, feature, or advantage of the present disclosure is to provide a biodegradable soil sensing system that is configured to detect the presence of a chemical or hazardous compound leak and wirelessly transmit an alert to a vehicle. Additionally, a distributed matrix of wireless in soil sensors applied with sufficient density across an area of interest and spatially correlated can provide of sufficient insight into soil stability. Routine observation of the relative position of nodes within a remote sensor network over time can provide insight into soil stability to indentify changes due to influences such as frost heave, compromised subsurface infrastructure, or environmental impacts to severe weather or seismic activity.

One or more of these and/or other objects, features or advantages of the present disclosure will become apparent from the specification and claims that follow.

DETAILED DESCRIPTION OF INVENTION

Embodiments in accordance with the present disclosure are set forth in the following text to provide a thorough understanding and enabling description of a number of particular embodiments. Numerous specific details of various embodiments are described below with reference to in soil sensors and the use of aerial vehicles, but embodiments can be used with other features. In some instances, well-known structures or operations are not shown, or are not described in detail to avoid obscuring aspects of the inventive subject matter associated with the accompanying disclosure. A person skilled in the art will understand, however, that the invention may have additional embodiments, or that the invention may be practiced without one or more of the specific details of the embodiments as shown and described.

Figure 1A:
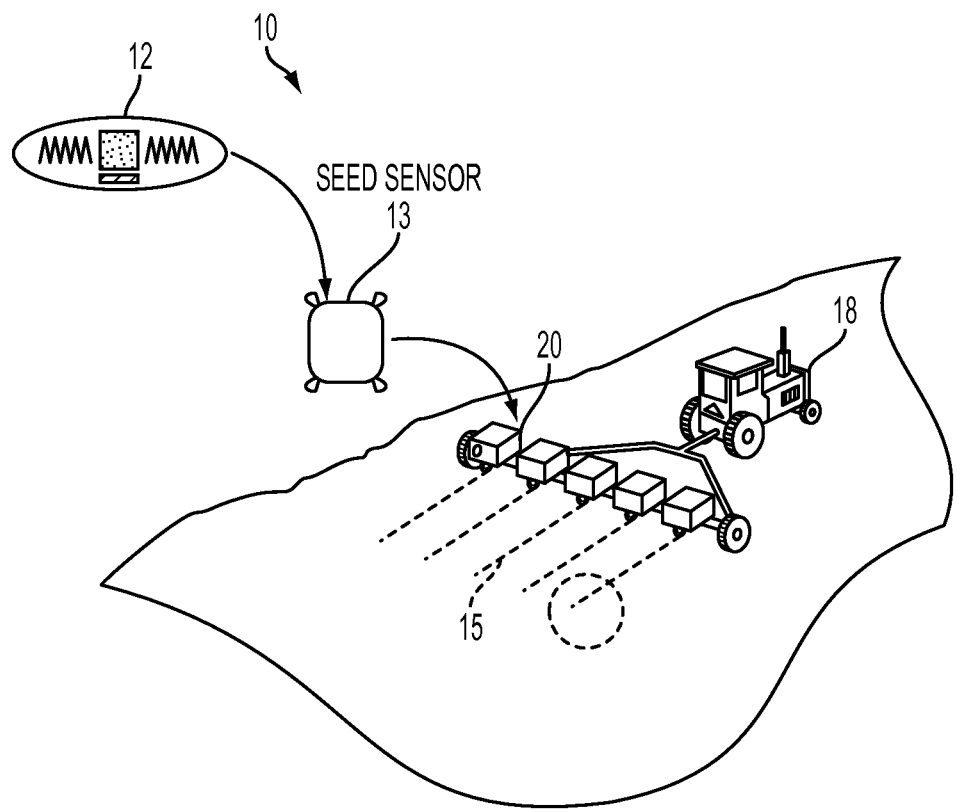
FIG. 1A is a diagram of the planting process in accordance with an embodiment of the invention.

Referring first to FIG. 1A, which shows a soil sensor 12 being deposited on a crop field in accordance with an embodiment of the invention 10. The biodegradable soil sensor 12 is of the type disclosed in patent number WO 2014/113460 A1 entitled Biodegradable Soil Sensor, Systems and Method, which is incorporated herein by reference in its entirety. A plurality of soil sensors 12 are mixed in with crop seed 13 and the sensors 12 and seeds 13 are placed in a seed dispenser 20 which is towed across the planting field by a vehicle 18. The seeds 13 and the sensors 12 are planted in rows 15 as required by the specific crop being grown. It should be noted that the method of planting the seed and soil sensor could take on many well known variations, all of which are fully contemplated by the invention.

Figure 1B:
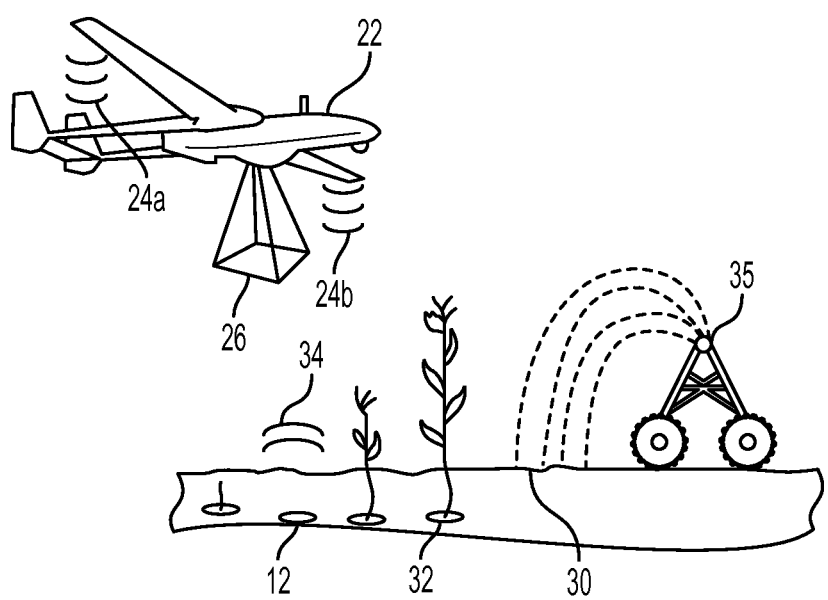
FIG. 1B is a diagram of the data retrieval process in accordance with an embodiment of the invention.

Referring now to FIG. 1B, which shows the crop field of FIG. 1A, after it has had time for the seeds 13 to grow into plants 32. In this figure, the soil sensor 12 is shown beneath the surface 30 of the field and is configured to measure data concerning the soil immediately surrounding the soil sensor 12 and transmit that data wirelessly through a wireless link 34. The soil sensor communications may be active transmissions or passively interrogated. The soil sensor 12 could be configured to measure for example, moisture level, nitrogen level or any characteristic or combination of characteristics that is desired in order to determine the condition of the soil.

An unmanned aerial vehicle (UAV) 22 is configured to fly over the field in a predetermined pattern and record geodetic high resolution imagery data 26 from the crop field using an imaging payload disposed on the UAV. Disposed on each wing of the UAV is a RFID interrogator array 24a and 24b which are configured to communicate with the soil sensors 12 using any wireless technique, with the preferred embodiment employing passive RFID. The RFID interrogator arrays 24a and 24b are set a predetermined distance apart on the UAV in order to leverage time/frequency domain difference of signal arrival from the seed sensor 12 in order to determine the relative location of a seed sensor to the UAV. In addition, preferably, the UAV will also have GPS capabilities so that the collected data from the sensors 12 and the geodetic imagery data 26 can be geodetically located and correlated into a high resolution map which indicates relatively precise location information. For more precise location information, the system could alternatively employ the use of augmented or differential GPS (DGPS) which would increase the positional accuracy of the measured data.

For illustration purposes only, an automated water sprinkler 35 is shown adjacent the crop field which may be programmed to apply corrective watering of the crops based on the analysis of the collected and correlated data. A water sprinkler 35 is shown for illustration purposes of a typical corrective action that may be required as a result of the collected data, but corrective actions could include for example a means for distributing fertilizer, pesticide or the like, based on the results of the data analysis.

Figure 2:
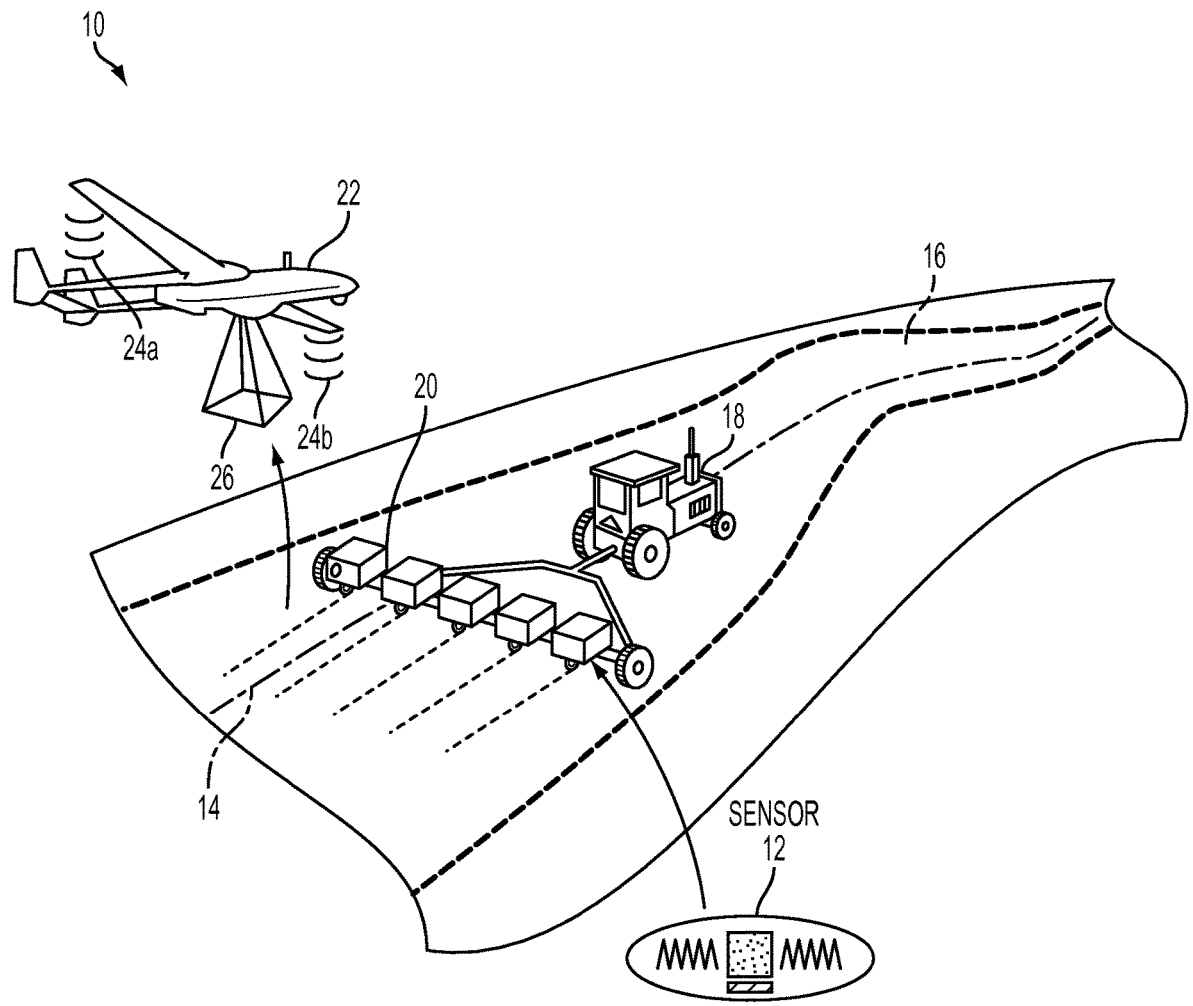
FIG. 2 is a diagram showing the chemical spill monitoring system in accordance with an embodiment of the invention.

Referring now to FIG. 2, where like numerals represent like features, a system for detecting chemical spills 10 is shown. In this embodiment, the soil sensor 12 is dispersed along the surface of right of way 16 that is adjacent a buried pipe-line 14. Similar to the system shown in FIG. 1A, the soil sensor 12 is configured to detect the presence of a chemical or chemicals in order to detect the occurrence of a leak from the pipe-line 14. The UAV 22 is programmed to fly over the pipeline in order to interrogate the soil sensors 12 using the RFID interrogator arrays 24a and 24b to detect the presence of a leak or spill. Again, the UAV 22 also has GPS or DGPS capability so that the collected data from the soil sensor 12 can be correlated with a specific location. Also the UAV 22 can record geodetic high resolution imagery data 26.

Figure 3:
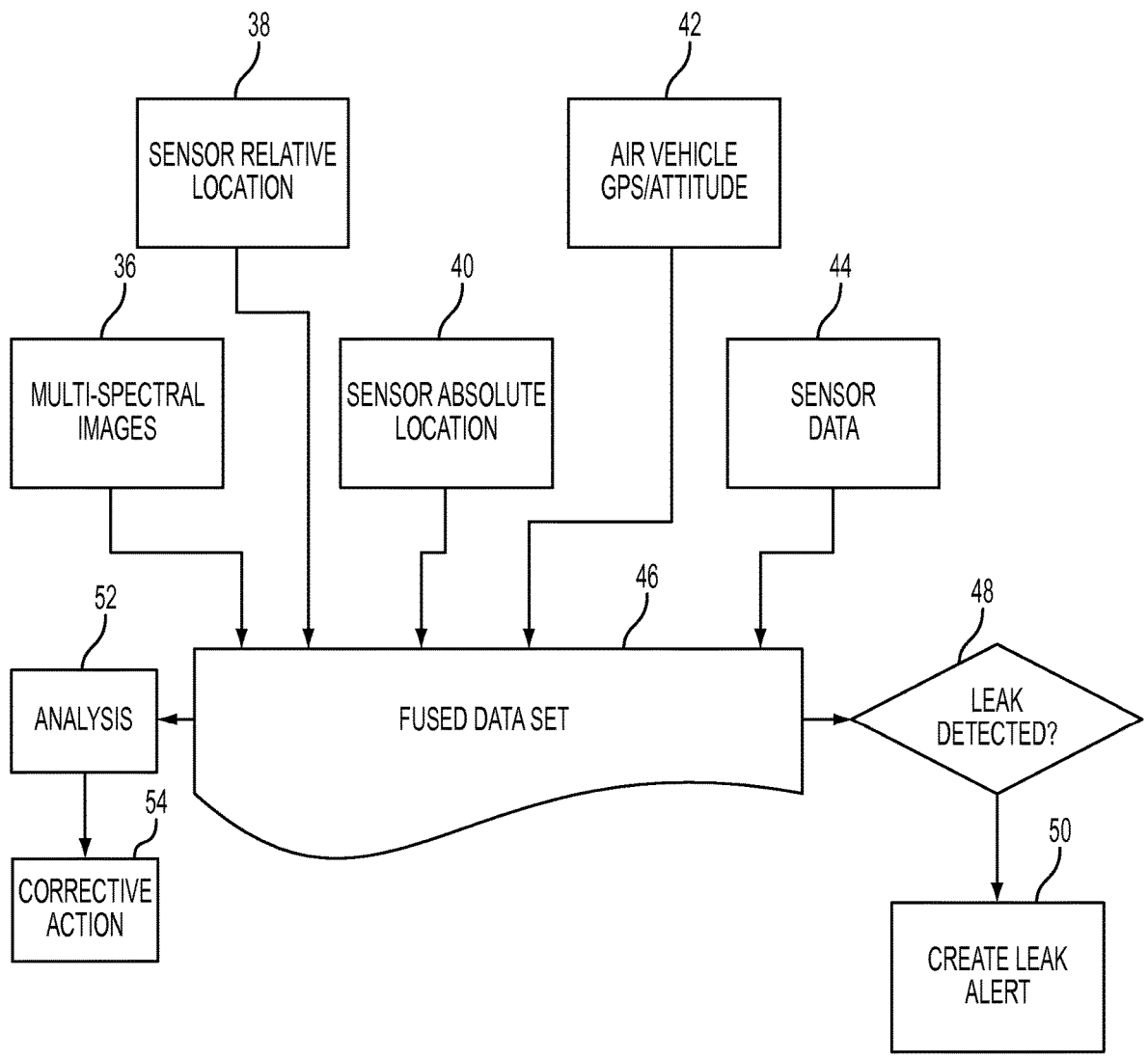
FIG. 3 is a simplified flow diagram showing the data analysis process of a crop field or chemical spill in accordance with an embodiment of the invention.

Referring now to FIG. 3, where a simplified flow diagram of the data fusion process for the data collection described in FIGS. 1A, 1B and 2 is shown. Multi-spectral image data 36 is acquired by a specially configured payload affixed to the UAV 22. This spectral image data 36 can include information concerning crop health. As discussed previously, seed sensor relative location data 38 is acquired which indicates where the seed sensor 12 is in relative location to the UAV 22. Combining this relative location data 38 of the seed sensor with the UAV GPS and altitude data 42 the seed sensor absolute location 40 can be determined. This information is combined with the seed sensor data 44. All the collected data is combined and a fused data set 46 may be created to generate an imagery mosaic with overlaid soil sensor data.

Depending on which scenario is being considered, in the case of the chemical spill alert process, the fused data 46 is analyzed to determine if a leak or spill has been detected at box 48. If a leak has been detected at box 48, an alert is created at box 50 which could include not only the location of the spill/leak, but also the size and severity of the spill/leak which will affect the appropriate corrective action response.

In the case of the agricultural process, the fused data set 46 will be correlated and analyzed at box 52 and based on this analysis a corrective action 54 may be required in order to improve crop health. As mentioned previously, the corrective action could be something like increased watering at specific locations of the crop field, or additional fertilizer could be applied in a predetermined area of the crop field.

I claim:

1. An in-soil data monitoring system comprising:
   a soil sensor disposed adjacent soil, wherein said soil sensor is configured to measure soil sensor data associated with a condition of the soil, and to transmit said soil sensor data; and
   an unmanned aerial vehicle, wherein said unmanned aerial vehicle is configured to passively interrogate said soil sensor in order to read said soil sensor data, and to determine relative location data pertaining to a relative location of said soil sensor to said unmanned aerial vehicle,
   wherein said soil sensor employs passive radio frequency identification (RFID) to wirelessly transmit said soil sensor data,
   wherein the system further comprises (i) a first RFID interrogator array disposed on a first wing of the unmanned aerial vehicle, and (ii) a second RFID interrogator array disposed on a second wing of the unmanned aerial vehicle, the first wing and the second wing extending in opposite directions, the first RFID interrogator array and the second RFID interrogator array being separated by a predefined distance, the first RFID interrogator array and the second RFID interrogator array being configured to wirelessly interrogate said soil sensor, and, having interrogated said soil sensor, to determine the relative location of said soil sensor to said unmanned aerial vehicle, and
   wherein said unmanned aerial vehicle is further configured:
      to perform a data fusion process on at least the relative location data and said soil sensor data to create a fused data set;
      to perform an analysis of the fused data set; and
      to determine an appropriate action to take relative to the condition of the soil based on the analysis of the fused data set.

2. The in-soil data monitoring system of claim 1, further comprising a GPS receiver disposed on said unmanned aerial vehicle, wherein said GPS receiver is configured to provide location information of said unmanned aerial vehicle.

3. The in-soil data monitoring system of claim 1, wherein said unmanned aerial vehicle is further configured to record geodetic high resolution imagery.

4. The in-soil monitoring system of claim 3, wherein said soil sensor data is associated with the condition of the soil in relation to growing crops.

5. The in-soil monitoring system of claim 4, wherein said soil sensor data is associated with the condition of the soil in relation to a chemical spill.

6. A method for improving the health of a crop comprising the steps of:

dispersing a plurality of in-soil sensors adjacent the crop, said sensors being configured to measure soil sensor data concerning the soil;

flying an unmanned aerial vehicle adjacent the crop, said unmanned aerial vehicle being configured to communicate with said plurality of in-soil sensors;

reading the soil sensor data from said plurality of in-soil sensors;

determining a location of an in-soil sensor of said plurality of in-soil sensors;

applying a corrective action to the crop based on the soil sensor data and the location of said in-soil sensor, wherein the determining of the location of said in-soil sensor includes:

affixing a pair of radio frequency identification (RFID) interrogators to said unmanned aerial vehicle, wherein affixing said pair of RFID interrogators to said unmanned aerial vehicle includes (i) disposing a first RFID interrogator array on a first wing of the unmanned aerial vehicle, and (ii) disposing a second RFID interrogator array on a second wing of the unmanned aerial vehicle, the first wing and the second wing extending in opposite directions, and the first RFID interrogator array and the second RFID interrogator array being disposed from each other by a predefined distance;

wirelessly interrogating, by each of the first RFID interrogator array and the second RFID interrogator array, said in-soil sensor to obtain the soil sensor data; and having interrogated said in-soil sensor, determining, by the first RFID interrogator array and the second RFID interrogator array, relative location data pertaining to a relative location of said in-soil sensor from said unmanned aerial vehicle based on a respective wireless signal received at each of the first RFID interrogator array and the second RFID interrogator array from said in-soil sensor; and operating said unmanned aerial vehicle to perform a data fusion process on at least the relative location data and said soil sensor data to create a fused data set, to perform an analysis of the fused data set, and to determine the corrective action to apply based on the analysis of the fused data set.

7. The method of claim 6, further comprising the step of affixing a GPS receiver to said unmanned aerial vehicle to determine a location of said unmanned aerial vehicle.

8. The method of claim 7, further comprising the steps of:
recording geodetic high resolution imagery of the crop from said unmanned aerial vehicle; and
correlating said geodetic high resolution imagery with the location of said in-soil sensor.

9. The in-soil data monitoring system of claim 1 wherein the RFID interrogators, when measuring the relative location of said soil sensor, are constructed and arranged:
to receive, at the first RFID interrogator array disposed on the first wing, a wireless signal at a first time;
to receive, at the second RFID interrogator array disposed on the second wing, the wireless signal at a second time; and
to determine the relative location of said soil sensor from the unmanned aerial vehicle based on a difference between the first time and the second time.

10. The method of claim 6 wherein determining the relative location of said in-soil sensor from said unmanned aerial vehicle includes:

receiving, at the first RFID interrogator array disposed on the first wing, a wireless signal at a first signal arrival time, receiving, at the second RFID interrogator array disposed on the second wing, the wireless signal at a second signal arrival time, and performing a relative location determination operation which determines the relative location of said soil sensor from said unmanned aerial vehicle based on a difference between the first signal arrival time and the second signal arrival time.

11. The method of claim 10 wherein dispersing the plurality of in-soil sensors adjacent the crop includes:
mixing the plurality of in-soil sensors with crop seed to form a sensor and crop seed mixture prior to planting the crop.

12. The method of claim 11 wherein dispersing the plurality of in-soil sensors adjacent the crop further includes:
after mixing, loading the sensor and crop seed mixture into a crop seed dispenser.

13. The method of claim 12 wherein dispersing the plurality of in-soil sensors adjacent the crop further includes:
after loading the sensor and crop seed mixture into the crop seed dispenser, operating the crop seed dispenser over a planting field to plant the sensors and the crop seed forming the sensor and crop seed mixture in the planting field.

14. The method of claim 13 wherein operating the crop seed dispenser includes:
planting the sensors and the crop seed in rows within the planting field.

15. The method of claim 14 wherein the sensors are fully biodegradable.

16. The in-soil data monitoring system of claim 1 wherein the pair of RFID interrogators disposed on said unmanned aerial vehicle outputs a wireless interrogation signal to the soil sensor to interrogate the soil sensor.

17. The in-soil data monitoring system of claim 16, wherein the soil sensor includes a transmitter which is powered by radio-frequency energy of the wireless interrogation signal that is output by the pair of RFID interrogators disposed on said unmanned aerial vehicle.

18. The in-soil data monitoring system of claim 17, wherein the transmitter of the soil sensor wirelessly transmits the data to the unmanned aerial vehicle in response to receiving the wireless interrogation signal.

19. The method of claim 6, wherein interrogating wirelessly the data from said in-soil sensor employing said RFID interrogators includes activating a transmitter of the in-soil sensor by transmitting an interrogation signal to the in-soil sensor from the unmanned aerial vehicle via the RFID interrogators.

20. The in-soil data monitoring system of claim 2, wherein said unmanned aerial vehicle is further configured to perform the data fusion process on at least the relative location data, said soil sensor data, and the location information of said unmanned aerial vehicle to create the fused data set.

21. The in-soil data monitoring system of claim 3 wherein the unmanned aerial vehicle is further configured:
to correlate said geodetic high resolution imagery with said soil sensor data to obtain correlated data;
to perform the data fusion process on at least the relative location data, said soil sensor data, and the correlated data to create the fused data set; and
to generate, from the fused data set, an imagery mosaic overlaid with said soil sensor data.

22. An in-soil data monitoring system comprising:
- a soil sensor disposed adjacent soil, said soil sensor being configured to measure soil sensor data associated with a condition of the soil, and to transmit said soil sensor data;
- an unmanned aerial vehicle configured to passively interrogate said soil sensor in order to read said soil sensor data, and to determine relative location data pertaining to a relative location of said soil sensor to said unmanned aerial vehicle,
- wherein the unmanned aerial vehicle includes a first wing, a second wing, a first RFID interrogator array disposed on the first wing of the unmanned aerial vehicle, and a second RFID interrogator array disposed on the second wing of the unmanned aerial vehicle, the first wing and the second wing extending in opposite directions, and the first RFID interrogator array and the second RFID interrogator array being separated by a predefined distance, the first RFID interrogator array and the second RFID interrogator array being configured to wirelessly interrogate said soil sensor, and, having interrogated said soil sensor, to determine the relative location of said soil sensor to said unmanned aerial vehicle, and
- wherein said unmanned aerial vehicle is further configured:
  - to perform a data fusion process on at least the relative location data and said soil sensor data to create a fused data set;
  - to perform an analysis of the fused data set; and
  - to determine an appropriate action to take relative to the condition of the soil based on the analysis of the fused data set.

* * * * *